US007663022B1

(12) United States Patent
Hudkins

(10) Patent No.: US 7,663,022 B1
(45) Date of Patent: Feb. 16, 2010

(54) TRANSGENIC BIOLUMINESCENT PLANTS

(76) Inventor: Bruce Eric Hudkins, 1723 S. Madison Ave., Tulsa, OK (US) 74120

(*) Notice: Subject to any disclaimer, the term of this patent is extended or adjusted under 35 U.S.C. 154(b) by 232 days.

(21) Appl. No.: 11/419,108

(22) Filed: May 18, 2006

Related U.S. Application Data

(63) Continuation-in-part of application No. 10/195,283, filed on Jul. 15, 2002, now Pat. No. 7,049,483.

(51) Int. Cl.
| | |
|---|---|
| C12N 15/82 | (2006.01) |
| C12N 15/84 | (2006.01) |
| C12N 15/31 | (2006.01) |
| C12N 15/53 | (2006.01) |
| C12N 15/62 | (2006.01) |
| A01H 5/00 | (2006.01) |

(52) U.S. Cl. .................. 800/282; 800/287; 800/288; 800/294; 800/300; 800/303; 435/8; 435/69.8; 435/189; 435/468; 435/469

(58) Field of Classification Search .................. None
See application file for complete search history.

(56) References Cited

U.S. PATENT DOCUMENTS

| | | | |
|---|---|---|---|
| 5,093,240 | A | 3/1992 | Inouye et al. |
| 5,162,227 | A | 11/1992 | Cormier |
| 5,221,623 | A | 6/1993 | Legocki et al. |
| 5,422,266 | A | 6/1995 | Cormier et al. |
| 5,583,024 | A | 12/1996 | McElroy |
| 5,723,765 | A | 3/1998 | Oliver et al. |
| 5,728,925 | A | 3/1998 | Herrera-Estrella et al. |
| 5,741,668 | A | 4/1998 | Ward et al. |
| 5,876,995 | A | 3/1999 | Bryan |
| 5,976,796 | A | 11/1999 | Szalay et al. |
| 6,247,995 | B1 | 6/2001 | Bryan |
| 7,049,483 | B1 | 5/2006 | Hudkins |
| 7,300,792 | B2 * | 11/2007 | Gupta et al. ............ 435/325 |
| 2005/0032033 | A1 | 2/2005 | Winterboer |

FOREIGN PATENT DOCUMENTS

| | | |
|---|---|---|
| EP | 0825257 | 8/1997 |
| WO | WO 97/40381 | 10/1997 |
| WO | WO 00/61740 | 10/2000 |
| WO | WO 03/042693 | 5/2003 |
| WO | WO 2004/006656 | 1/2004 |

OTHER PUBLICATIONS

Kirchner et al. Gene 81(2): 349-354 (1989).*
Urwin et al. The Plant Journal 24(5): 583-589 (2000).*
Meighen, E. The FASEB Journal 7: 1016-1022 (1993).*
Kado, C. pp. 179-180 and 192-196 In: Microbial Genome Methods, Adolph, K., ed., CRC Press: Boca Raton (1996).*
Okumura, K. World Journal of Microbiology and Biotechnology 8: 638-644 (1992).*
Sanseverino, J. Applied and Environmental Microbiology 71(8): 4455-4460 (2005).*
Edward A. Meighen, "Bacterial Bioluminescense: organization, regulation and application of the *lux* genes", pp. 1016-1022.
Clarence I. Kado, "Live Time Quantification of Bacterial Interactions In Various Environments", pp. 179,180, 192-196.
K. Okumura, "Enhanced Stable Expression of a Vibrio Luciferase Under The Control of the Translational Enhancer in Transgenic Plants", pp. 638-644.
John Sanseverino, "Use of *Saccharomyces cerevisiae* BLYES Expressing Bacterial Bioluminescence for Rapid, Sensitive Detection of Estrogenic Compounds", pp. 4455-4460.
Greer, L.F. et al. Imaging of Light Emission from the Expression of Luciferases in Living Cells and Organisms: A Review. Luminescence. Wiley, Chichester, GB, vol. 17, No. 1, Jan. 2002, pp. 43-74.
Francis, K. et al. Monitoring bioluminescent *Staphylococus aureus* infections in living mice using a novel *luxABCDE* construct. Infection and Immunity. American Society for Microbiology, Washington, U.S., vol. 68, No. 6, Jun. 2000, pp. 3594-3600.
Matsuo et al. Plant Biotechnology 18(1): 71-75 (Mar. 2001).
Nass et al. Planta 212(2): 149-154 (2001).
Plieth et al. pp. 252-253. In: Plant-Nutrition—Food Security and Sustainability of Agro-Ecosystems, Horst et al., eds., Kluwer Academic Publishers: The Netherlands (2001).
Mayerhofer et al. The Plant Journal 7(6): 1031-1038 (1995).
Kumar et al. FEBS Letters 268(1): 287-290 (Jul. 1990).
Knight et al. Journal of Cell Biology 121(1): 83-90 (Apr. 1993).
Illarionov et al. pp. 223-249 In: Methods in Enzmology, vol. 305, Academic Press (2000).
Millar et al. The Plant Cell 4: 1075-1087 (Sep. 1992).
Barauh-Wolff et al. The Plant Cell Reports 18(9): 715-720 (1999).
Paul T. Toran; "Transgenic Methods: The Illuminating Power & Controversy"; www.bio.davidson.edu/people/kamernd/seminar/2002/edibile/pt.htm.
Keiko Gomi, "Molecular Cloning and Expression of the cDNAs encoding Luciferin-Regenerating Enzyme From *Lucioloa cruciata* and *Luciola lateralis*", Gene 294 (2002) 157-166.
XP-002372778, www.interauct.com/news/main2000.html.

* cited by examiner

*Primary Examiner*—David T Fox
(74) *Attorney, Agent, or Firm*—Head, Johnson & Kachigian, P.C.

(57) ABSTRACT

Transgenic plants, and a method for making the same, wherein genes encoding the enzyme luciferase and its corresponding substrate luciferin are incorporated into a native plant genome. Once transformed into plant cells, these genes may be regulated such that under certain endogenous or exogenous conditions, their expression in the mature plant results in bioluminescence. Different luciferin/luciferase complexes and/or mechanisms of regulation may be utilized for these transgenic plants, depending on a variety of factors such as plant species and the circumstances under which a bioluminescent reaction is desired. Phototransformation may be utilized to vary the wavelength of light emitted from the mature plant.

48 Claims, 2 Drawing Sheets ns Ser. No. 10/195,283 filed Jul. 15, 2002, now U.S. Pat. No. 7,049,483, incorporated in its entirety herein by reference.

STATEMENT REGARDING FEDERALLY SPONSORED RESEARCH OR DEVELOPMENT

Not Applicable.

REFERENCE TO A SEQUENCE LISTING, A TABLE, OR A COMPUTER PROGRAM LISTING COMPACT DISC APPENDIX

See Sequence Listing, attached hereto.

BACKGROUND OF THE INVENTION

1. Field of the Invention

The present invention relates to transgenic bioluminescent plants. More specifically, the present invention relates to plants, cells of which have been transfected via *Agrobacterium* or other means known to those in the art, with nucleic acid molecules encoding luciferase and luciferin such that the resulting plant luminesces, in whole or in part. The transfected nucleic acid molecules may be operably linked to, and their expression regulated by, promoters in order to control the incidence, timing and duration of the genetically engineered bioluminescence. Bioluminescent emissions may further be transformed such that light of varying wavelengths is emitted from the plants.

2. Prior Art

It has been known in the art for some time that a certain class of enzymes, known as luciferases, will bioluminesce in the presence of compatible substrates, referred to generally as luciferins. Luciferases are a broad class of proteins that exhibit little homology and are found in terrestrial and marine bacteria, jellyfish, fireflies and a variety of other organisms. Nucleic acid molecules which encode luciferase have been identified, and their bioluminescent activities have been used extensively to study gene regulation and expression. By inserting luciferase protein encoding sequences downstream from a promoter to be studied, one may easily tell when that promoter has been activated by the resulting bioluminescence.

Luciferins, the substrates for luciferases, tend to be complex organic molecules. Bacterial luciferins, such as those found in *Vibrio, Photobacterium* and *Xenorhabdus,* have been described as a complex of fatty acid reductase proteins. Some luciferins are thought to be formed by means of complex catabolic pathways. Others, such as the jellyfish luciferin coelenterazine, result from the cyclization of amino acids of a polypeptide. Until recently, nucleic acid molecules encoding the luciferin complex were not known. This meant that in order to detect luciferase, luciferin had to be applied directly to organisms expressing luciferase. The luciferin had to be absorbed by the target, and as a result, suitable hosts were generally limited to cells, relatively thin tissue cultures, and very small seedlings. Organisms or cells expressing luciferase were lysed and exposed to a luciferin solution. This obviously killed the host organism.

There has been a significant amount of work done to improve the use of luciferase in studying gene expression; however, all efforts have been limited by the inability to produce in vivo bioluminescence without the addition of chemicals, outside of a laboratory environment, and in larger organisms.

U.S. Pat. No. 5,093,240 to Inouye et al., incorporated by reference, discloses the transgenic use of the jellyfish luciferase known as aequorin and derivatives thereof. This patent also discloses the use of a luciferase enzyme in a vector designed for mass production. The patent suggests that large quantities of luciferase may be grown in bacterial culture. The patent does not disclose nucleic acid molecules which produce intracellular luciferin. Nor does it contemplate or disclose suitable methods for inserting sequences that encode luciferin into a plant cell.

U.S. Pat. No. 5,162,227 to Cormier, incorporated by reference, also discloses recombinant DNA vectors into which a sequence encoding luciferase has been inserted. As with the above referenced patent, it contemplates use of these vectors for mass production of luciferase in bacterial culture. It further contemplates use of the luciferase gene as a marker or selection gene sequence. It does not, however, contemplate the insertion of a luciferin coding sequence into the vector, in vivo bioluminescence, or the formation of a vector suitable for transfection of plant cells.

U.S. Pat. No. 5,422,266 to Cormier et al., incorporated by reference, discloses an invention very similar to the one described in the above paragraph. It discloses the insertion of a luciferase gene into a vector suitable for use in microorganisms. Like the above mentioned patent, it contemplates neither the additional insertion of a luciferin coding sequence, in vivo bioluminescence, nor the use of vectors suitable for insertion into plant cells.

U.S. Pat. No. 5,583,024 to McElroy et al., incorporated by reference, discloses use of a second luciferase that is useful in transcription assays. This patent contemplates using the luciferase to quantify transcription of various promoter sequences. It requires lysis, and thus death, of the transformed cells. It does not contemplate either in vivo bioluminescence or the use of a luciferin encoding sequence.

U.S. Pat. No. 5,976,796 to Szalay et al., incorporated by reference, discloses a fusion protein comprising a luciferase and a fluorescing protein. This patent contemplates the use of the fusion protein as a double marker in transcription assays. It does not provide for intracellular luciferin or in vivo bioluminescence.

U.S. Pat. No. 5,221,623 to Legocki et al., incorporated by reference, discloses the use of the lux bacterial luciferase gene in transcription assays of various promoters. It does not contemplate in vivo bioluminescence in mature plants or the use of a luciferin encoding sequence. Furthermore, the lux bioluminescence mechanism requires a substantial concentration of organic aldehydes, and this patent discloses applying aldehyde vapors to the microorganisms. This would be impractical for use in the present invention.

U.S. Pat. Nos. 5,876,995 and 6,247,995 B1 to Bryan, both incorporated by reference, disclose the use of bioluminescent luciferase/luciferin mechanisms for use in a wide variety of novelty items. These patents do not disclose recombinant uses for luciferase/luciferin recombinant DNA. Nevertheless, the specifications of these patents are very useful in that they give a very detailed, textbook-like description of the entire field of bioluminescence.

U.S. Pat. No. 5,741,668 to Ward et al., incorporated by reference, discloses a polypeptide capable of spontaneously forming, in vivo, the luciferin coelenterazine. This patent further discloses the mass production of coelenterazine by expressing appropriate coding sequences in bacterial cultures and harvesting the resulting proteins. It does not contemplate combining luciferin coding sequences with those for luciferase in a single vector and using that vector to form bioluminescent organisms such as mature plants.

It is therefore desirable to provide a method for causing bioluminescence in a mature multicellular organism, such as a plant.

It is also desirable to provide a method for inducing bioluminescence without the need to apply chemicals to an organism.

It is also desirable to provide for a mature plant capable of bioluminescence outside of a laboratory setting and without the need of applying special chemicals.

It is also desirable to provide a mature plant capable of bioluminescence where the timing of that bioluminescence is controlled, or when such bioluminescence can communicate important information about the relative health or condition of the plant.

It is also desirable to provide a mature plant capable of bioluminescence where the bioluminescent emission can be transformed and the wavelength of the light emitted from the plant can vary.

BRIEF SUMMARY OF THE INVENTION

The present invention relates to the use of bioluminescent mechanisms to create transgenic organisms, such as multicellular plants, capable of bioluminescence. There are foreseeable advantages to bioluminescent plants such as food crops. Crops capable of producing light facilitate night-time harvesting. Once harvested, they would eventually cease to glow. Hence, crops could be harvested at any time, including during the cooler evening hours. This facilitates harvest and lengthens the period of time when harvest is possible. Another advantage is that controlled bioluminescence can be used to communicate critical information about the relative health or condition of crops, such as temperature and ripeness, as well as stressors such as drought, disease, infestation or lack of nutrients.

Alternatively, the present invention could be applied to common house and landscaping plants, as the present invention enhances the aesthetic qualities of landscape vegetation.

In order to facilitate bioluminescence in plants, at least two coding sequences must be added. The first is a sequence encoding a luciferase enzyme; the second encodes its substrate, luciferin. There are many different types of luciferase found in nature. Different luciferases have different luciferins as their substrates, and appropriate pairings of luciferin and luciferase are known to the skilled artisan.

Luciferases and their corresponding luciferins have been found in bacteria, fireflies, jellyfish and other sea life. For years, these combinations have been used by scientists to study gene regulation and expression in a variety of organisms. Luciderases serve as excellent markers because of the ease with which their expression may be detected.

In current genetic expression assays involving bioluminescence, a luciferase coding sequence is engineered downstream from a promoter region to be studied. This recombinant DNA is then inserted into a vector which is subsequently used to transform a plant, animal or bacterial cell. Depending upon promoter activity, the luciferase gene either will or will not be expressed. Transformed cells are then lysed in an appropriate bioluminescence buffer and luciferin is added. Qualitative and/or quantitative bioluminescence data may then be obtained, such as by measuring emission spectra. If the sample luminesces, it means that the promoter region has induced expression. Those skilled in the art will appreciate that these are common expression assays.

Until recently, methods of in vivo production of luciferins were unknown. This is why cells had to be lysed and luciferin added thereto. Recently, however, as disclosed in U.S. Pat. No. 5,741,668 to Ward et al., the metabolic pathway for the formation of the luciferin coelenterazine was elucidated. Coelenterazine is the substrate for a small group of luciferases found in jellyfish. In light of this discovery, a luciferin could be produced within a living cell. Accordingly, organisms susceptible to transformation may now be induced to bioluminesce, by using appropriate nucleic acid molecules.

In accordance with the present invention, bacterial luciferase and luciferin (components of the lux operon) are expressed within plant cells. To accomplish this, coding sequences for compatible bacterial luciferase and luciferin are inserted into plant cells by means of transformation or transfection well known in the art. Preferably, expression of these genes and the resulting bioluminescence will occur only within the leaves of transformed plants. One method of restricting expression to leaf cells is to include upstream promoter regions specific only to leaf cell expression. Somatic or other plant cells that have been successfully transfected are grown to mature plants. The process of producing mature plants from individual plant cells is well known in the art.

Promoters, including some that adhere to the circadian clock, are likewise well known to those skilled in the art. A 5' promoter sequence, such as NOS, 35S, RuBisCO, or CAB2 may be inserted upstream of the luciferase and luciferin coding regions. Some promoters are down-regulated at night, meaning that promoted genes will also be down-regulated in the dark. This prevents the expression of the inserted genes from placing undue stress on the plant. Because luciferins tend to be fragile organic molecules having a half life of one and a half to two hours, the bioluminescent activity of the plant will cease within three to four hours after dusk.

In some cases, it may be desirable to utilize one or more different 5' promoters to regulate expression of specific genes. Specifically, it may be desirable to use a promoter that induces expression only in the dark. This would result in the bioluminescence beginning at night and ending at dawn. Those skilled in the art will appreciate that there a large variety of promoters that cause downstream expression conditions. Stress-linked plant promoters, those that induce expression under certain conditions such as drought, disease, infestation or lack of nutrients, are likewise well known. Examples of stress-linked promoters include cat (catalase that is sensitive to peroxides), adh (a general stress-linked promoter in plants that is sensitive to anoxia or oxidants), and hsp/gst (heat shock protein that is sensitive to heavy metals in the soil). Selection of the most desirable promoter or promoters will depend on the plant variety as well as additional factors unique to the situation under consideration and need not be elucidated here.

Bioluminescence may be dependent upon or enhanced by the presence of substances such as oxygen. It may therefore be desirable to have the luciferase and luciferin peptides targeted to specific organelles within the transformed plant cell. Those skilled in the art will appreciate that there are a variety of known target sequences that may be added to the N-terminus of a polypeptide. This is done by inserting a polynucleotide sequence coding for a targeting sequence at the 5' end of the coding sequence. When this is expressed, the target sequence will be included in the translated polypeptide. The target sequence will then direct the polypeptides to a specific organelle. This may be desirable in order to ensure that any required co-factors are present. In addition, all polypeptides function at an optimum pH. Certain organelles may have an internal pH more conducive to the bioluminescence reaction. Various organelles may also provide an environment that improves the stability of the polypeptides. Those skilled in the art will realize that these are only some of many factors that may influence the direction of the luciferase and luciferin to specific organelles.

Those skilled in the art will also appreciate that it may be desirable to add one or more additional sequences to the vector or vectors used for transfection. Some promoters used to regulate the inserted bioluminescent genes may require other proteins in order to be activated or deactivated. It is often desirable with transfection vectors to include a selection sequence. Selection sequences code for genes that confer resistance to various antibiotics such as ampicillin, kanamycin, hyrgromycin and streptomycin. Such selection sequences are generally used to isolate cells that have been successfully transfected. However, bioluminescence can also be used as an indicator for selection and it is not necessary to use a selection sequence. Cells that have been successfully transfected may be induced to bioluminesce and may therefore picked out of cells that have not been transfected. It may be desirable to include additional sequences, such as those which encode transporter proteins, or any other desired protein.

Phototransformation is likewise well known in the art, and by incorporating into the present invention a gene encoding a phototransforming or wave-shifting protein, light of varying wavelengths may be emitted from the bioluminescent plant. This further enhances the utility of the present invention disclosed herein.

DETAILED DESCRIPTION OF THE INVENTION

Figure 1:
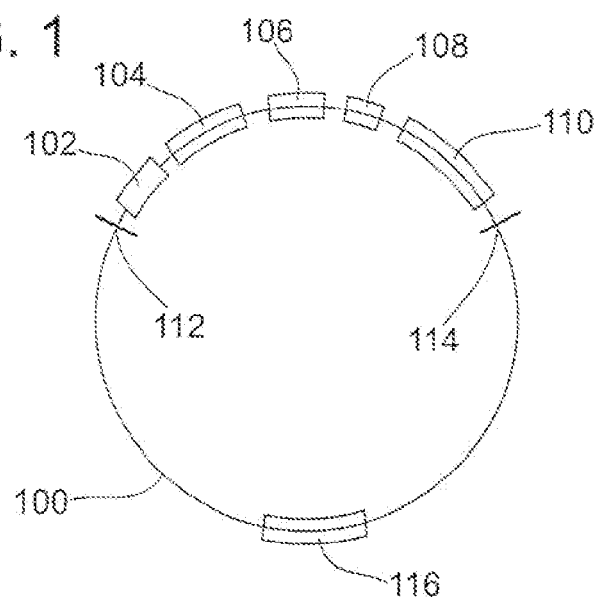
FIGS. 1, 2 and 3 are diagrammatic views of each of the three recombinant DNA plasmids constructed in the disclosed embodiment.

In describing the present invention, the following terminology will be used in accordance with the definitions set out below. This terminology is well known to those skilled in the art.

"Polynucleotide" refers to a polymeric form of ribonucleotides or deoxyribonucleotides of any length. This term refers only to the primary structure of the molecule. Thus, the term includes double- and single-stranded DNA, as well as double- and single-stranded RNA. It also includes modified (modification, for example, by methylation, phosphorylation, and/or capping) and unmodified forms of the polynucleotide.

"Recombinant polynucleotide" refers to a polynucleotide of genomic cDNA, of semisynthetic or synthetic origin, which by virtue of its origin or manipulation: (1) is not associated with all or a portion of the polynucleotide with which it is associated in nature; and/or (2) is linked to a polynucleotide other than that to which it is linked in nature; or (3) does not occur in nature.

"Replicon" refers to any genetic element, e.g., a plasmid, chromosome, virus, etc., that behaves as an autonomous unit of polynucleotide replication within a cell, i.e., capable of replication under its own control.

"Vector" as used herein refers to a replicon in which another polynucleotide segment is attached, so as to bring about the replication and/or expression of the attached segment. Vectors may have one or more polynucleotide or recombinant polynucleotide and one or more control sequences. Vectors as used herein always include a promoter in operable linkage with one or more coding sequences. In the present invention, "vectors" include plasmids.

"Control sequence" refers to polynucleotide sequences which are necessary to effect the expression and/or secretion of coding sequences to which they are ligated. The nature of such control sequences differs depending upon the host organism. In prokaryotes, such control sequences generally include a promoter, a ribosomal binding site, and a terminator. In eukaryotes, such control sequences generally include promoters, terminators and, in some instances, enhancers. In addition, in both prokaryotes and eukaryotes, some control sequences direct the expressed polypeptide to a particular location within the cell or region within a multicellular organism. The term "control sequences" is intended to include, at a minimum, all components whose presence is necessary for expression, and may also include additional polynucleotide sequences that influence the expression of a protein.

"Promoter" refers to a polynucleotide sequence upstream from an expressed polynucleotide. A promoter sequence signals the cellular machinery to express the polynucleotide downstream from it. Promoters, a subclass of control sequences, may be required in order for a polynucleotide to be expressed. There are many known promoters. Some promoters operate like a switch and only signal a cell to express a downstream polynucleotide under certain conditions, such as when the organism is under insect or pathogenic attack. Which promoter is best for a given transgenic organism will depend on the desired level of expression and the type of organism being transformed, as well as the circumstances under which expression is desired. Examples of promoters known to persons skilled in the art are those which regulate expression depending upon exogenous conditions such as temperature, ambient daylight or time of day, as well as those which correspond with endogenous conditions such as disease, dehydration or infestation within the host organism.

"Host cells", "microbial cells", "cells" and other terms denoting microorganisms or higher eukaryotic cell lines cultured as unicellular entities, are used interchangeably, and refer to cells which can be, or have been, used as recipients for recombinant vectors or other transfer polynucleotides, and include the progeny of the original cell which has been transfected. It is understood that the progeny of a single parent cell may not necessarily be completely identical in morphology or in genomic or total DNA complement as the original parent, due to accidental or deliberate mutation. Progeny of the parental cell which are sufficiently similar to the parent and which can be characterized by a relevant property, such as the presence of a nucleotide sequence encoding a desired peptide, are included in this definition and are covered by the above terms.

"Transformation" or "transfection" refers to the insertion of an exogenous polynucleotide into a microbial cell, or cells of a multicellular organism such as a plant, irrespective of the method used for insertion. (For example, insertion via direct uptake, transduction, f-mating, particle bombardment or bacteria-mediated gene transfer.) The exogenous polynucleotide may be maintained as a non-integrated vector such as a plasmid, or alternatively, may be integrated into the host genome.

"Polypeptide" refers to the amino acid product of a sequence encoded within a polynucleotide, and does not refer to a specific length of the product. Thus, peptides, oligopeptides, and proteins are included within this definition. This term does not refer to post-expression modifications of the polypeptide, for example, glycosylation, acetylation, phosphorylation, sialylation, and the like. The polypeptides may be so modified, however.

"Transforming polynucleotide" refers to any of a number of polynucleotide structures known in the art and used for transforming cells. They include, but are not limited to, plasmids, phagemids, cosmids, and bacterial artificial chromosomes (BACs). They include Ti plasmids and other structures capable of transforming plant cells, as well as other types of cells.

"Luciferase" refers to any of a wide variety of enzymes that oxidize a corresponding luciferin, thereby causing bioluminescence. The present invention is generally drawn to luciferases found in bacteria. The term luciferase also refers to oxidizing enzymes found in fireflies, fish, squid and other organisms capable of bioluminescence.

"Luciferin" refers to compounds and their precursors, some of which are derived from oligopeptides, which are susceptible to oxidation by a luciferase or are otherwise required for the bioluminescence reaction. In the particular embodiment described below, luciferin from the bacterial lux operon specifically includes those fatty acid reductase polypeptides encoded by the lux genes which are utilized in the synthesis of substrate for the bioluminescent reaction. Those skilled in the art will appreciate that any luciferin that may be successfully produced inside a plant cell with a corresponding luciferase will be suitable for the invention. Luciferins may be found in bacteria, fish, jellyfish, squid and other organisms, all of which are incorporated herein.

"Selection sequence" refers to any of a number of polynucleotide sequences that may be placed in a vector to allow successfully transfected cells to be distinguished from cells that have not been transfected. An example of such a selection sequence is a polynucleotide sequence coding for a promoter which confers kanamycin resistance. Those skilled in the art will appreciate that there are a variety of sequences that encode for antibiotic resistance and are commonly used to select transfected cells. Those skilled in the art will also appreciate that there are selection sequences other than those that encode for antibiotic resistance.

"Sterility operon" refers to one or more genes added to a transfection vector that cause a plant or other organism to be incapable of reproduction. Those skilled in the art will appreciate that a successful sterility operon has been developed by and is currently being used by Monsanto Corporation in their ROUNDUP READY™ soybeans. Those skilled in the art will also appreciate that this is only one of many methods of inducing sterility within a plant or other organism. Such methods are described in U.S. Pat. Nos. 5,723,765, 6,297,426 and 6,228,643, all of which are incorporated by reference.

Those skilled in the art will appreciate that, in addition to the wide variety of vectors available for the techniques described herein, there are also a wide variety of control sequences that may be added to a polynucleotide sequence. It is possible that in some or all plants, bioluminescence will be enhanced by directing the luciferase and corresponding luciferin to a specific location within the plant. This may be accomplished using control sequences that result in the addition of amino acids at either the N- or C-termini of the proteins. These added amino acids utilize mechanisms within a plant to direct the protein to which they are attached to specific regions of the plant cell. For example, some control sequences direct proteins to the chloroplasts, while others result in the protein being attached to a membrane. The techniques of utilizing theses control sequences to direct a certain protein to a certain location are well known to those skilled in the art.

It is also well known to those skilled in the art that control sequences may also be used to regulate both the translation and transcription of a polynucleotide sequence. These control sequences may be employed to regulate the concentration of the protein within the organism that is expressing it. The addition of these various types of control sequences to any given vector is a relatively simple procedure.

Some control sequences require the inclusion of a second, regulatory sequence. For example, some control sequences inhibit gene translation only when an inhibitor protein is present. In this situation, it is necessary to add to the vector a sequence that encodes the inhibitor protein. This inhibitor protein sequence may in turn have its own control sequences up- or downstream from it. It is even possible for an inhibitor protein sequence to have a control sequence that itself requires a second inhibitor protein sequence in order to function properly. In addition, just as there are control sequences that require inhibitor proteins, there are also control sequences that require activation proteins that increase gene translation. These control sequences require the addition of an activation protein sequence.

There are also control sequences that regulate expression of coding sequences at the transcription stage. These sequences inhibit or facilitate ribosomal activity on mRNA. All of these mechanisms are well known to those skilled in the art.

The selection of particular control sequences, promoters and vectors to be used for a particular plant will be depend on the method of transformation, the plant into which the vector is being introduced, and personal discretion.

The present invention relates to the use of two or more nucleotide sequences to construct a bioluminescence mechanism within plant cells. Under conditions suitable for expression, such as darkness, drought or infestation, the resulting mature plants will luminesce for a given time period. Depending upon the aim of the invention, it may be preferable to have the plant luminesce throughout the evening or for at least a few hours following dusk.

The present invention may be applied to any type of plant, and is especially desirable in food crops, landscaping and houseplants. Trees, shrubs, flowers and grass are desirable plants for use in the present invention. These are plants typically found in the landscaping of a home's curtilage, where increased security and pleasant appearance are highly desirable. Both monocotyledons such as grasses and palms, and dicotyledons such as trees and most flowers, may be used in the present invention. Current plant transformation techniques, discussed below, now provide a means for genetically modifying any type of plant.

Bacterial luciferases have been identified in a number of species of bacteria. Among them are the genera *Vibrio, Photobacterium,* and *Xenohabdus* Once a suitable luciferase/luciferin bioluminescence mechanism has been chosen, such as the lux operon from *Vibrio fischeri* described in detail below, appropriate nucleotide sequences are assembled into one or more vectors or plasmids which are in turn utilized to transform or 'transfect' plant cells. Those skilled in the art will appreciate that there are a number of methods for transfecting a eukaryotic cell such as a plant cell. One of the most common of these is to utilize a bacterial plasmid derived from *Agrobacterium tumefaciens* or *Agrobacterium rhizogenes*. The *Agrobacterium* plasmid contains a T-DNA segment that it transfers into the chromosome of a plant cell it has infected.

The T-DAN of the wild type bacterium may be replaced with a polynucleotide up to 25 Kb long.

In the present invention, genes for luciferase and for luciferin, as well as other proteins, promoters, targeting sequences, selection sequences and control sequences may be inserted in place of the T-DNA. This insertion may occur via a single transformation or by way of two or more serial transformations, depending upon the quantity of DNA ultimately being inserted. Transfection of target plant cells by *Agrobacterium* will then result in plant cells in which the desired polynucleotide sequences have been incorporated into the plant's native genome. By exposing the plant cell to appropriate amounts of hormones and nutrients, a fully mature plant may be developed from the single transfected cell.

The *A. tumefaciens* plasmid only transfects dicotyledon cells, thus limiting its use. However, *A. rhizogenes* has been found to successfully transfect monocotyledon cells utilizing a similar plasmid. Those skilled in the art will appreciate that different types of plant cells may require different types of plasmids and/or *Agrobacteria* in order to successfully transfect the respective plant cells.

Other methods for transforming plant cells exist. In the art of biolistics, metal microparticles are coated with the desired recombinant DNA. This recombinant DNA may be the same polynucleotide described above. The DNA-coated microparticles are then accelerated using gunpowder, helium gas or other methods known to those skilled in the art, to a velocity such that they may penetrate the plant cell. One of the advantages to biolistics is that it can be utilized on any plant cell. Micro-injection is another method of transforming plants. A microscopic needle is utilized to penetrate, and inject DNA directly into, the nucleus of the target plant cell.

Another transformation method suitable for all plant cell types is electroporation. Electroporation involves shocking the plant cells with a powerful electric pulse, momentarily disrupting the cell membrane and causing pores to form therein. Recombinant polynucleotides in the surrounding solution then enter the plant cell through these pores.

Yet another method of transforming plant cells is to expose them to polyethylene glycol (PEG). Exposure of plant cell protoplasts to PEG makes them momentarily permeable. Like electroporation, this allows the DNA in a surrounding solution to simply seep into the cell.

Those skilled in the art will appreciate that there are still other methods of transforming plant cells, including the use of silicone fibers. The selection of the most suitable method of transformation will depend on a variety of factors known to those skilled in the art. Such factors include, but are not limited to, the type of plant cell being transformed, the type of luciferase and luciferin genes being utilized, the size of the recombinant DNA molecule to be inserted, the available facilities, and the relative expense of each method.

Bacterial artificial chromosomes (BACs) may be used to transform plant cells with recombinant polynucleotide fragments up to 350 Kb long. Furthermore, the Ti plasmid from *Agrobacterium rhizogenes* has been found to successfully transfect monocotyledon cells. Binary vectors, like pBIN20, are plasmids that contain the Ti plasmid and bordering sequences, allowing them to also transfect plant cells.

In plant cells transformed and grown into a mature plant, the bioluminescent mechanism encoded by the recombinant DNA will be expressed subject to any associated promoter or promoters and will cause the plant to bioluminesce.

In the preferred embodiment of the present invention, three separate plasmids are constructed, replicated in *E. coil,* and independently transfected or incorporated into a native *Agrobacterium* genome using electroporation, and the resulting *Agrobacterium* plasmids are subsequently utilized to transfect plant cells. Those skilled in the art will appreciate that vector and plasmid design and construction may vary, particularly in relation to the amount or quantity of recombinant DNA to be transfected. Plasmid design and construction for the disclosed embodiment is as follows:

Plasmid pLuxAB/pUCD2715

For this construct, the luxAB fusion gene (SEQ ID NO: 10) and plasmid pUCD2715 are utilized as described by Clarence I. Kado, "Live Time Quantification of Bacterial Interactions in Various Environments", Microbial Genome Methods, 192-194 (Kenneth W. Adolph, Ed.)(CRC Press, 1996), and Okumura et al., "Enhanced Stable Expression of a *Vibrio* Luciferase Under the Control of the Ω-translational Enhancer in Transgenic Plants", World Journal of Microbiology and Biotechnology 9:638-644 (November 1992), which publications are incorporated herein by reference.

With respect to FIG. 1, plasmid pLux AB/pUCD2715 100 includes the NOS promoter 102, which regulates the expression of the hph gene 104, which encodes resistance to the antibiotic hygromycin for selection of the plasmid in plant cells. 35S promoter 106 regulates the expression of the luxAB fusion gene 110. Situated between them is the Ω-3 translational enhancer 108. Origin of replication region 114 contains sequences recognized by DNA polymerase for replication of plasmid pLuxAB/pUCD2715 100 in an *E. coli* culture, while origin of replication region 112 contains sequences for replication in *Agrobacterium*. Plasmid pLuxAB/pUCD2715 100 further includes selection sequence 116, which encodes resistance to the antibiotic kanamycin for selection of the plasmid in *Agrobacterium*.

Optionally, a targeting sequence may be cloned into plasmid pLuxAB/pUCD2715 100. This targeting sequence preferably codes for an additional peptide sequence that is added to the N-terminus of the luciferase enzyme encoded by the luxAB fusion gene 110. This targeting sequence causes the intracellular machinery to direct the luciferase enzyme to a specific organelle or region of the cell. The targeting sequence may direct proteins to a variety of organelles including, but not being limited to, the Golgi apparatus, mitochondria, chloroplasts, lysosomes, peroxisomes, or the nucleosome. In the absence of a targeting sequence, the luciferase/luciferin bioluminescence reaction will go forward in the cytosol. However, targeting the enzyme and its substrate to a specific organelle may be advantageous for a number of reasons. Various organelles may have optimal internal pH or higher concentrations of oxygen ATP, or other co-factors to facilitate the luciferase/luciferin reaction. Furthermore, directing all of the luciferase and luciferin to a selected organelle will result in a higher relative concentration of the enzymes and accelerate the reaction. This has the result of shortening the length of time it takes to consume the luciferin, but it also increases the brightness of the bioluminescent plant.

Plasmid pLuxC[ires]D

Persons skilled in the art will appreciate that an internal ribosome entry site (IRES) facilitates the expression of multiple genes in eukaryotic cells using a single promoter. A known synthetic IRES, synthesized by Midland Scientific, Inc. of Omaha, Nebr. and described by Ivanov et al., "A tobamovirus genome that contains an internal ribosome entry site functional in vitro", Virology 232(1):32-43 (May 1997) has the following sequence (SEQ ID NO: 1):

GGATCCGTCGACGAATTCGTCGATTCG-
GTTGCAGCATTTAAAGCGGTT GACAACTT-
TAAAAGAAGGAAAAAGAAGGTTGAA-
GAAAAGGGTGTAGT
AAGTAAGTATAAGTACAGACCGGAGAAG-
TACGCCGGTCCTGATTCGTT TAATTTGAAA-
GAAGAAAATGTCCCGGGCTGCAG

This IRES is cloned into pGEM®-3Z (PROMEGA CORP., Madison, Wis.) between the PstI and BamHI restriction sites, thus forming an intermediate construct "pIRES".

The luxC gene is PCR® amplified from the p607 plasmid (which contains the entire lux operon; see Kado, supra and Okumura et al., supra; used with permission) using the following primers:
C Forward (SEQ ID NO: 2) GGTCTAGACAGTT-
TAAAAAAGCAGTCT
C Reverse (SEQ ID NO: 3) GGGGATCCCTTGATGAT-
GTGATCAATCG The amplification product is then cut with XbaI and with BamHI, and cloned into the 35S-CaMV cassette (JOHN INNES CENTRE, NORWICH, UK) between the XbaI and BamHI restriction sites, thus forming an intermediate construct "p35S-C-CaMV".

The luxD gene is amplified from p607 using the following primers:
D Forward (SEQ ID NO: 4) GGCCCGGGTGTCCCAT-
AGTTAAAGGAAA
D Reverse (SEQ ID NO: 5) GGGAATTCATTC-
CTTTTTGGTGATTCTG This amplification product is then cloned into the pBlue-TOPO™ (INVITROGEN CORP., Carlsbad, Calif.) vector using a topoisomerase cloning protocol, thus forming an intermediate construct "pBlue-D".

The cloned luxD gene is excised from "pBlue-D" using HindIII and cut into "pIRES" using HindIII. The resulting plasmid, a construct entitled "pIRES-D", can be verified by cutting with EcoRI and analyzing restriction fragments.

The IRES-luxD sequence is cut out of "pIRES-D" using EcoRI and cloned into "p35S-C-CaMV" using EcoRI. The resulting construct is "p35S-C-IRES-D-CaMV" and can be verified by cutting with SacI and analyzing restriction fragments.

The "p35S-C-IRES-D-CaMV" sequence is excised from the cassette using EcoRV and moved into plasmid pGreenI 0029 (JOHN INNES CENTRE, NORWICH, UK) using EcoRV, thus completing the pLuxC[ires]D plasmid. The pLuxC[ires]D plasmid is grown in E. coli cultures using methods and materials that are well known in the art.

Figure 2:
Figure 2:
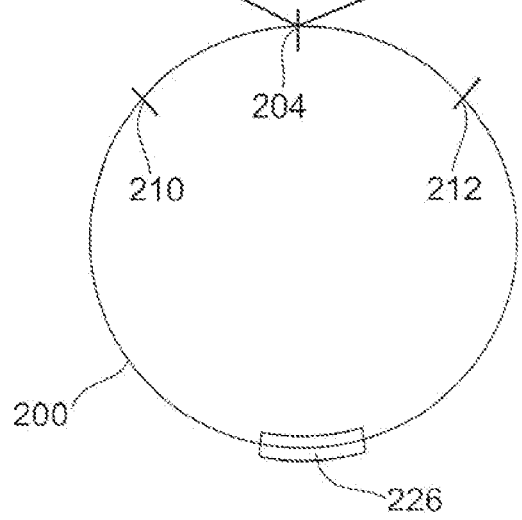

With respect to FIG. 2, plasmid pLuxC[ires]D 200 is comprised of a cloning region 202 flanked by a left border 206 and a right border 208. Left border 206 and right border 208 each correspond to a BgIII restriction site 204 for the insertion or excision of cloning region 202. 35S promoter 214 regulates expression of the luxC gene 216, the internal ribosome entry site 218, and the luxD gene 220. NOS promoter 222 regulates the downstream expression of selection sequence 224. Selection sequence 224 encodes resistance to the antibiotic geneticin for selection of the plasmid in plant cells. The nptI (neomycin phosphotransferase) gene 226 encodes resistance to the antibiotic kanamycin for selection of the plasmid in Agrobacterium. Origin of replication region 212 contains sequences recognized by DNA polymerase for replication of plasmid pLuxC[ires]D 200 in an E. coli culture, while origin of replication region 210 contains sequences for replication in Agrobacterium.

Plasmid pLuxE[ires]Frp

The luxE gene is amplified from p607 using the following primers:
E Forward (SEQ ID NO: 6) GGCTCGAGTTAGGTAT-
TACTGGAGAGGG
E Reverse (SEQ ID NO: 7) GGGTCGACTGAAACTC-
TACCATCAACAA The amplification product is then cut with XhoI and with SalI
The frp gene from Vibrio harveyi is amplified using the following primers:
frp Forward (SEQ ID NO: 8) GGCTGCAGGCTC-
CCAATAAATGCCGTTA
frp Reverse (SEQ ID NO: 9) GGACTAGTTGGCAGCG-
TATGGTCAAAAT The amplification product is then cut with PstI and SpeI.
Both of these products are then cloned into intermediate vector pCR-TOPO™ (INVITROGEN CORP., Carlsbad, Calif.). The luxE gene is excised from the intermediate vector using XhoI and EcoRI, and cloned into a NOS cassette (JOHN INNES CENTRE, NORWICH, UK) using XhoI and EcoRI, thus forming intermediate construct "pNOS-E".

The frp gene is excised from the intermediate vector using PstI and HindIII and cloned into "pIRES" (see plasmid pLuxC[ires]D above), thus forming intermediate construct "pIRES-Frp", which is in turn cut with EcoRI and cloned into "pNOS-E" using EcoRI. This results in a construct having the sequence "pNOS-E-IRES-Frp", which is excised from its cassette using EcoRV and cloned into plasmid pGreenII 0179 (JOHN INNES CENTRE, NORWICH, UK), to complete the pLuxE[ires]Frp plasmid. The pLuxE[ires]Frp plasmid is grown in E. coli cultures using methods and materials that are well known in the art.

Figure 3:
Figure 3:
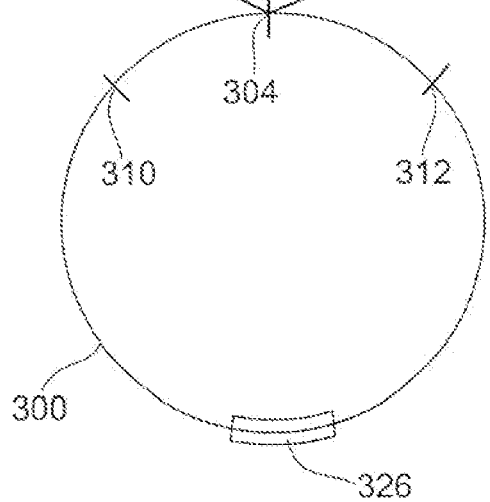

With respect to FIG. 3, plasmid pLuxE[ires]Frp 300 is comprised of a cloning region 302 flanked by a left border 306 and a right border 308. Left border 306 and right border 308 each correspond to a BgIII restriction site 304, for the insertion or excision of cloning region 302. NOS promoter 314 regulates expression of the luxE gene 316, the internal ribosome entry site 318, and the frp gene 320. 35S promoter 322 regulates the downstream expression of selection sequence 324. Selection sequence 324 encodes resistance to the antibiotic hygromycin for selection of the plasmid in plant cells. The nptI (neomycin phosphotransferase) gene 326 encodes resistance to the antibiotic kanamycin, for selection of the plasmid in Agrobacterium. Origin of replication region 312 contains sequences recognized by DNA polymerase for replication of plasmid pLuxC[ires]D 200 in an E. coli culture, while origin of replication region 310 contains sequences for replication in Agrobacterium.

Those skilled in the art will appreciate that there are many known or potential modifications of the individual vectors and plasmids, including the Agrobacterium plasmid, as described herein. Accordingly, the actual restriction sites and restriction endonucleases to be utilized will be determined by the precise plasmid used. The choice of plasmid makes no difference. It is generally desirable to use different restriction sites on the 5' and 3' ends of insert recombinant DNA. This prevents plasmids from ligating to themselves without incorporating a recombinant DNA sequence.

Transfection of Plasmids into Agrobacterium and Transfection of Plant Cells

Figure 4:
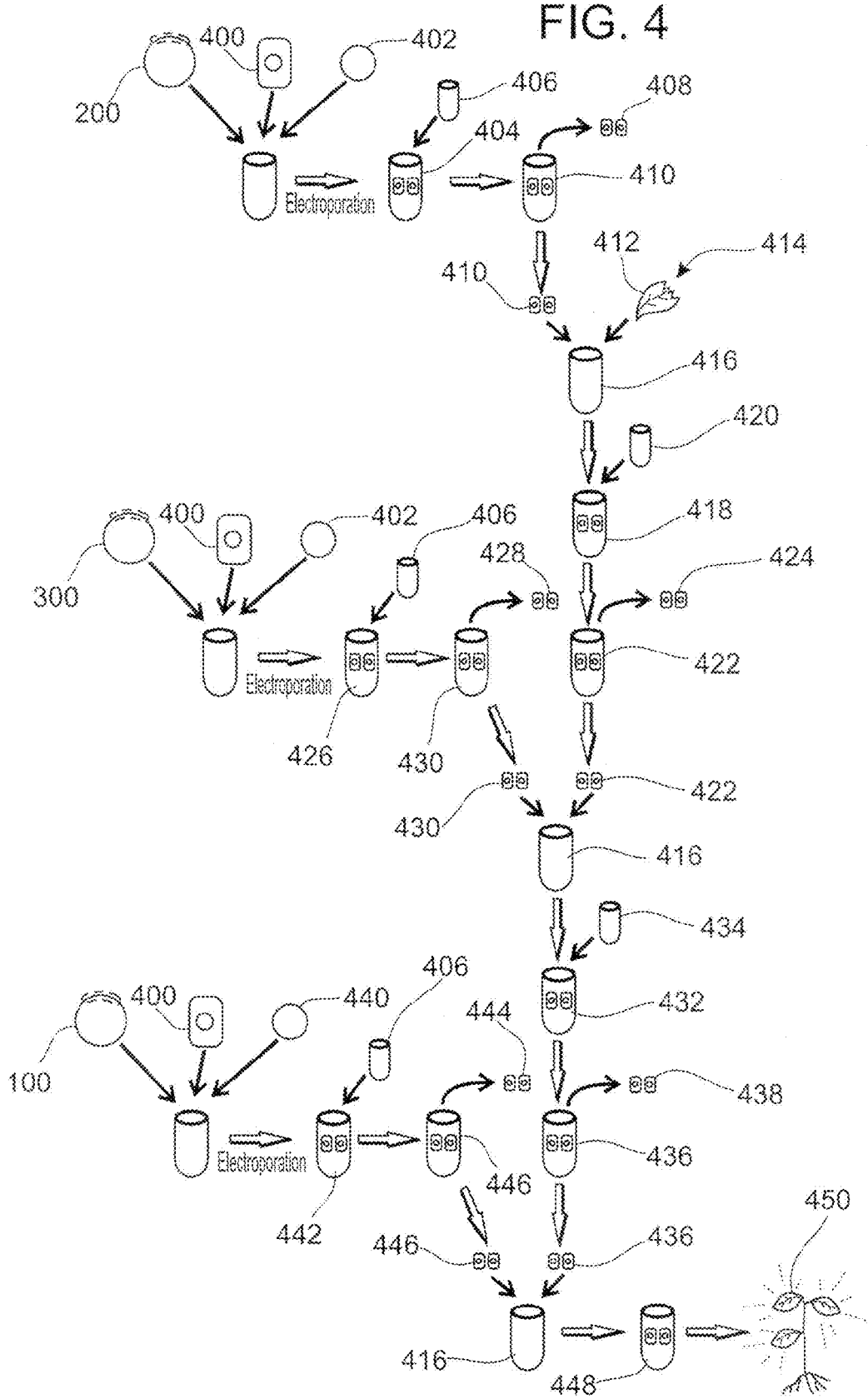
FIG. 4 is a diagrammatic view of the disclosed method for transfecting the desired recombinant DNA sequences into *Agrobacterium* and subsequently into intermediate plant cell cultures or calli and ultimately into a callus that will become the mature plant.

With respect to FIG. 4, plasmid pLuxC[ires]D 200 is transfected into a suitable Agrobacterium 400 along with helper plasmid pSoup 402 (JOHN INNES CENTRE, NORWICH, UK) via electroporation, using standard electroporation protocols well known in the art. Those skilled in the art will further appreciate that transfection will occur in a suitable buffer or other medium. The transfected *Agrobacterium* cells 404 are subjected to an appropriate amount of the antibiotic kanamycin 406, which selects for successful transfection. Negatively selected cells 408 are those which succumb to kanamycin 406. Successfully transfected *Agrobacterium* cells 410 remain in culture.

Successfully transfected *Agrobacterium* cells 410 are combined with a leaf fragment 412 having a torn portion 414 in a callus growth medium 416. The resulting callus 418 is subjected to an appropriate amount of the antibiotic geneticin 420, which selects for successfully transfected plant cells 422. Negatively selected plant cells 424 are those which succumb to geneticin 420.

Plasmid pLuxE[ires]frp 300 is transfected into a suitable *Agrobacterium* 400 along with helper plasmid pSoup 402 (JOHN INNES CENTRE, NORWICH, UK) via electroporation, using standard electroporation protocols well known in the art. Those skilled in the art will further appreciate that transfection will occur in a suitable buffer or other medium. The transfected *Agrobacterium* cells 426 are subjected to an appropriate amount of the antibiotic kanamycin 406, which selects for successful transfection. Negatively selected cells 428 are those which succumb to kanamycin 406. Successfully transfected *Agrobacterium* cells 430 remain in culture.

Successfully transfected *Agrobacterium* cells 430 are combined with successfully transfected plant cells 422 in a callus growth medium 416. The resulting callus 432 is subjected to an appropriate amount of the antibiotic hygromycin 434, which selects for successfully transfected plant cells 436. Negatively selected plant cells 438 are those which succumb to hygromycin 434.

Plasmid pLuxAB/pUCD2715 100 is transfected into a suitable *Agrobacterium* 400 along with helper plasmid pUCD2614 (see Kado, supra.) 440 via electroporation, using standard electroporation protocols well known in the art. Those skilled in the art will further appreciate that transfection will occur in a suitable buffer or other medium. The transfected *Agrobacterium* cells 442 are subjected to an appropriate amount of the antibiotic kanamycin 406, which selects for successful transfection. Negatively selected cells 444 are those which succumb to kanamycin 406. Successfully transfected *Agrobacterium* cells 446 remains in culture.

Successfully transfected *Agrobacterium* cells 446 are combined with successfully transfected plant cells 436 in a callus growth medium 416. Selection with hygromycin is optional, as successfully transfected mature plant may otherwise be selected on the basis of bioluminescence. The resulting callus 448 is grown into a mature transgenic plant 450 using techniques well known in the art. It will be appreciated that this diagram is a simplification of the process and that there are many steps involved and it may take several weeks or months to develop a mature plant. In the case of transgenic trees and large shrubs, it may be several years before a mature transgenic bioluminescent plant develops.

Those skilled in the art will recognize that the promoter regions selected may be any of a number of known promoter sequences. For example, certain known promoters down-regulate a downstream sequence when night falls. This means, for example, that the luciferase could stop being expressed around dusk. Down-regulating the foreign sequence allows the plant to conserve its energy, amino acids and ribosomes for natural functions. It is possible to utilize other promoters that are never turned off, i.e. constitutive promoters. It is also possible to utilize promoters that up-regulate at night and down-regulate during the day, as well as stress-linked promoters which regulate expression under certain endogenous conditions such as drought, infestation or disease. It is known in the art that there are a number of promoter regions relating to the circadian clock that regulate expression according to the amount of sunlight to which they are exposed. Because the bioluminescence of these plants can only be seen in the dark, it is preferred that such bioluminescence be regulated by the amount of light exposure. This is not necessary, however, and any appropriate promoter may be used. In flowering plants, it may be desirable to induce bioluminescence in the flowers themselves. Alternatively, it may be desirable in fruiting plants to induce bioluminescence only in the fruit. Plant promoters known in the art include CAB2, RuBisCO, NOS, and 35S.

LuxC 216, luxD 220 and luxE 316 encode polypeptides that help synthesize the aldehyde substrate required for the bioluminescene reaction. Those skilled in the art will appreciate that other luciferins may require a different metabolic pathway and therefore an operon of one or more different genes in order to form intracellular luciferin. Those skilled in the art will further appreciate that the present invention may be comprised of operons of varying complexity. As is also known in the art and described herein, the use of an alternative luciferin would require use of an alternative corresponding luciferase.

In the disclosed embodiment, luxC 216 and luxD 220 are regulated by a 35S promoter 214. In an alternative embodiment, these genes are regulated by a circadian clock promoter that turns off in the nighttime. As such, bioluminescencein this particular embodiment will only last a few hours after dusk. It may be desirable to utilize a promoter that turns on at dusk. It may also be preferable to utilize a promoter that is not dependent upon the circadian clock, such as a stress-linked promoter.

The lux operon had originally been thought to be ineffective in plant cells. This is due, in part, to the lack of available flavin mononucleotide (FMN) that is not bound to flavoproteins and is both free within the cytosol and is present in its reduced state. $FMNH_2$ is a required co-factor for the lux bioluminescence reaction. A number of approaches may be taken to ensure that adequate $FMHN_2$ is present in the cytosol. In the present invention, a flavin reductase gene frp 320 is incorporated into cloning region 302 of plasmid pLuxE[ires]Frp 300. Frp 320 may come from any known source, preferably from the bacterium *Vibrio harveyi*. Frp 320 and luxE 316 are introduced into *Agrobacterium* by way of a common plasmid pLuxE[ires]Frp 300, along with an internal ribosome entry site 318, but those skilled in the art will appreciate that vector and plasmid design and selection may vary.

Frp 320 and luxE 316 are downstream from promoter region 314. These genes may be regulated by the same or a different promoter than promoter region 214 (regulating luciferase). In the disclosed embodiment, luxE 316 and frp 320 are regulated by the NOS promoter. It is generally desirable that the FMN reductase protein be expressed in an amount sufficient to provide adequate amounts of $FMNH_2$ to facilitate bioluminescence. Those skilled in the art will appreciate that over-expression of the FMN reductase protein may disrupt intracellular chemistry.

Another method of regulating the amount of intracellular $FMNH_2$ is to include within the transforming polynucleotide an operon encoding the proteins necessary for $FMNH_2$ catabolism. Appropriate promoter sequences may be used in order to provide an adequate amount of free $FMNH_2$ in the cytosol. This operon may or may not include an FMN reductase gene.

Yet another method of providing free $FMNH_2$ in the cytosol is to include in the transforming polynucleotide a control sequence that up-regulates the native $FMNH_2$ catabolic pathway within the plant cell. This up-regulating control sequence may itself be regulated by a promoter region that controls the degree of up-regulation of the native $FMNH_2$ catabolism operon.

This particular embodiment also includes an hph gene 104 (hygromycin resistance), a geneticin selection sequence 224 and a hygromycin selection sequence 324 for selection of the respective plasmids in plant cells, and a kanamycin selection sequence 116 and nptI gene 226/326 (hygromycin) for selection of the respective plasmids in *Agrobacterium*. Those skilled in the art will appreciate that these are representative of several possible selection sequences. Other ubiquitous antibiotic resistance selection sequences include those that confer resistance to ampicillin or streptomycin. Those skilled in the art will also appreciate that the hph gene 104 in pLuxAB/pUCD2715 100 is not necessary per se, because bioluminescence of the mature plant may itself serve as the selection marker for successful transfection of the luciferase gene. It is still possible to use antibiotic resistance or other selection markers, if desired.

It may be desirable to ensure that these transgenic bioluminescent plants are sterile. Persons who oppose the genetic modification of organisms may be more accepting of these plants if they are incapable of reproducing. Those skilled in the art will appreciate that methods for making genetically modified organism sterile have already been developed. Such methods are described in U.S. Pat. Nos. 5,723,765, 6,297,426 and 6,228,643, referred to supra. Those skilled in the art of embryology will appreciate that there are several promoter sequences regulated by the organism's age. When plants first sprout, a number of promoters are turned on or off. Several active promoters will eventually be turned off as the plant ages, while inactive promoters will be turned on over time. Recombinant polynucleotides having genes to be inserted into a plant's genome may include a sterility operon that is activated by an early development promoter region. This would cause the sterility operon to induce production of a toxin which would kill the seedling. This would prevent the plant from producing offspring. One such toxin is ribosomal inhibitory protein (RIP), which is well known in the art.

Not all luciferin catabolic pathways have been elucidated. However, those skilled in the art will realize that there are a variety of methods to accomplish this. One preferred method is the utilization of a genomic library. For example, the entire genome of a particular species may be chopped into several shorter strands of DNA. Chromosomes are mixed with one or more restriction enzymes, resulting in the chromosomes being cut into many strands of DNA. The restriction enzymes are then deactivated by denaturation or other methods known in the art. The DNA strands are then inserted into plasmids, phagemids, cosmids or BACs. Those skilled in the art will recognize that this process is commonly used to form genomic libraries of various species.

Individual plant cells may be cultured in a petri dish, liquid media or other means known in the art. They are then transformed with the Ti plasmid or other methods as described above. This transformation is utilized to insert DNA coding for a luciferase protein. Using control sequences, such as kanamycin resistance disclosed above, is a common method for selectively growing transformed plant cells. Successfully transformed plant cells are capable of expression luciferase.

A CAB2 promoter, temperature-sensitive promoter, or other means may be used to regulate transcription and translation of the luciferase gene. Those plant cells having the luciferase gene inserted in them may then be transformed a second time, using the genomic library created by the method described above. It will be obvious to those skilled in the art that the luciferase used in the initial transformation of the plant cells must come from the same species from which the DNA library is derived. Those skilled in the art of bioluminescence are aware that luciferases from various species are generally incompatible with luciferins from other species.

A control sequence located within the plasmid, phagemid, cosmid or BAC used to make the genomic library is preferably different from the control sequence used in the initial transformation. For example, if the initial plasmid possesses kanamycin resistance, it would be preferable if the second polynucleotide sequence to be transformed encodes resistance to another antibiotic such as gentamycin. The twice-transformed plant cells may then be grown in media containing both kanamycin and gentamycin such that it is selected only for plant cells that contain both plasmids. This results in selection for plants that have incorporated within them a luciferase gene and a portion of genomic library. Those skilled in the art will appreciate that it is likely that the operon coding for the luciferin catabolic pathway is present in at least one of these twice-transformed plant cells. The plant cells are then grown under conditions that provide for expression of the luciferase gene and the genes of the genomic library. Any plant cells that catabolize luciferin will bioluminesce. These plant cells may then be grown into mature plants that bioluminesce.

Alternatively, it may be desirable to isolate plant cells that bioluminesce and identify the polynucleotide sequence responsible for luciferin catabolism. Once the luciferin catabolism operon has been isolated, it may be incorporated into the same plasmid, phagemid, cosmid or BAC as the original luciferase gene. This new transforming polynucleotide may then be used to transform plant cells, thereby providing bioluminescing plant cells by means of a single transformation. The cells may then be grown up into mature plants that bioluminesce.

In yet another alternative embodiment of the present invention, the bioluminescent plant may be further genetically engineered to express a phototransformative protein such as green fluorescent protein (GFP) from the jellyfish *Aequorea victoria*. To accomplish this, a suitable DNA sequence encoding the desired phototransformative protein is inserted into the plant's native genome using techniques well known in the art and discussed in detail above. Phototransformation is likewise well known in the art. "Phototransformative protein" herein refers to any of a number of proteins that have the ability to capture and modify photons from a bioluminescent light source in such a way that light of a different wavelength is emitted. Other phototransformative proteins include those encoded by luxF and luxG from the bacterial lux operon, as well as known mutants, variants or analogs of GFP, including GFP isolated from the sea pansy, *Renilla reniformis*. GFP has been described as noncovalently binding to the luciferase/luciferin complex in jellyfish, but the purpose for changing the wavelength of bioluminescence is unknown. Generally speaking, the Forster energy transfer effect is believed to allow for a highly efficient conversion of blue light to green light.

GFP is a well known reporter that has been successfully expressed in a wide variety of organisms. GFP absorbs blue light, such as that emitted from known bioluminescence pathways, and emits green light by means of fluorescence. Variants have slightly different excitation and emission peaks within the visible spectrum. The gene encoding GFP can be regulated with promoters, including stress-linked promoters described above, such that it is only expressed under certain conditions. Those skilled in the art will appreciate that the regulated emission of green light in the disclosed bioluminescent plant, either in lieu of or in addition to bioluminescence, serves as yet another means of communicating information about conditions either endogenous or exogenous to the plant. Moreover, green fluorescence may itself be utilized to screen or select those plants which have been successfully transfected with GFP. Alternatively, successful transfection of GFP may be determined via an accompanying selection sequence conferring resistance to an antibiotic.

Whereas, the present invention has been described in relation to the drawings attached hereto, it should be understood that other and further modifications, apart from those shown or suggested herein, may be made within the spirit and scope of this invention.

What is claimed is:

1. A method for making a transgenic bioluminescent plant, comprising the steps of:

selecting from a foreign genome at least one lux gene encoding a luciferase and at least one lux gene encoding a luciferin that is compatible with said luciferase, wherein said foreign genome contains a lux operon;

constructing at least one vector using a first plasmid, a second plasmid and a third plasmid, wherein said at least one vector comprises at least one light inducible promoter for regulation of expression of said lux genes, wherein said first plasmid comprises luxA and luxB, said second plasmid comprises luxC and luxD, and said third plasmid comprises luxE and frp, wherein said frp encodes a flavin reductase;

transfecting at least one plant cell with said at least one vector, wherein said at least one plant cell is selected from the group consisting of a monocotyledon cell and a dicotyledon cell; and growing said at least one plant cell into a mature plant.

2. The method of claim 1 further comprising the step of incorporating said vector into said first, second and third plasmids using electroporation.

3. The method of claim 1 further comprising the step of deriving said first, second and third plasmids from an *Agrobacterium*.

4. The method of claim 3 wherein said *Agrobacterium* is selected from the group consisting of *Agrobacterium tumefaciens* and *Agrobacterium rhizogenes*.

5. The method of claim 1 wherein said foreign genome is that of a bacterium selected from the group consisting of genera *Vibrio, Photobacterium,* and *Xenorhabdus*.

6. The method of claim 1 wherein said frp gene is selected from a second foreign genome.

7. The method of claim 6 wherein said second foreign genome is that of *Vibrio harveyi*.

8. The method of claim 1 wherein said at least one of said second and third plasmids further comprises an internal ribosome entry site.

9. The method of claim 1 wherein said at least one light inducible promoter for regulation of expression is a 5' promoter selected from the group consisting of the RuBisCO 5' promoter and the CAB2 promoter.

10. The method of claim 1 wherein said at least one vector further comprises a sterility operon that renders mature plants incapable of reproduction.

11. The method of claim 1 wherein said at least one vector further comprises a targeting sequence such that expressed polypeptides are directed to a specific organelle.

12. The method of claim 1 wherein said at least one vector further comprises at least one selection sequence comprising at least one gene conferring resistance to an antibiotic.

13. A transgenic bioluminescent plant, comprising:
at least one plant cell comprising at least one recombinant DNA, wherein said at least one plant cell is selected from the group consisting of a monocotyledon cell and a dicotyledon cell; and
wherein said at least one recombinant DNA comprises at least one lux gene encoding a luciferase, at least one lux gene encoding a luciferin that is compatible with said luciferase, and at least one light inducible promoter for regulation of expression of said lux genes; and
wherein said lux genes are selected from a foreign genome containing a lux operon.

14. The plant of claim 13 wherein said foreign genome is selected from the group of bacteria consisting of genera *Vibrio, Photobacterium,* and *Xenorhabdus*.

15. The plant of claim 13 wherein said at least one lux gene encoding a luciferase comprises luxA and luxB, and said at least one lux gene encoding a luciferin comprises luxC, luxD and luxE.

16. The plant of claim 13 wherein said recombinant DNA further comprises at least one gene encoding a flavin reductase.

17. The plant of claim 16 wherein said gene encoding a flavin reductase is an frp gene selected from a second foreign genome.

18. The plant of claim 17 wherein said second foreign genome is that of *Vibrio harveyi*.

19. The plant of claim 13 wherein said recombinant DNA further comprises at least one internal ribosome entry site.

20. The plant of claim 13 wherein said at least one light inducible promoter for regulation of expression of said genes is a 5' promoter selected from the group consisting of the RuBisCO 5' promoter and the CAB2 promoter.

21. The plant of claim 13 wherein said recombinant DNA further comprises a sterility operon that renders the plant incapable of reproduction.

22. The plant of claim 13 wherein said recombinant DNA further comprises a targeting sequence such that expressed polypeptides are directed to a specific organelle.

23. The plant of claim 13 wherein said recombinant DNA further comprises a selection sequence comprising at least one gene conferring resistance to an antibiotic.

24. The plant of claim 13 wherein said recombinant DNA further comprises at least one gene encoding a phototransformative protein and at least one means for regulation of expression of said gene encoding a phototransformative protein.

25. The plant of claim 24 wherein said gene encoding a phototransformative protein is a lux gene selected from the group of bacteria consisting of genera *Vibrio, Photobacterium,* and *Xenorhabdus*.

26. A method for making a transgenic bioluminescent plant, comprising the steps of:
transfecting at least one plant cell with a vector comprising at least one light inducible promoter operably linked to at least one of a lux gene encoding a luciferase and a lux gene encoding a luciferin that is compatible with said luciferase; and
growing said at least one plant cell into a mature plant.

27. The method of claim 26 further comprising the step of selecting said lux genes from a foreign genome containing a lux operon.

28. The method of claim 27 wherein said foreign genome is that of a bacterium selected from the group consisting of genera *Vibrio, Photobacterium,* and *Xenorhabdus*.

29. The method of claim 26 wherein said vector further comprises at least one gene encoding a flavin reductase.

30. The method of claim 29 wherein said vector comprises a first plasmid having luxA and luxB, a second plasmid having luxC and luxD, and a third plasmid having luxE and frp.

31. The method of claim 30 wherein said at least one of said second or third plasmids further comprises an internal ribosome entry site.

32. The method of claim 26 wherein said light inducible promotor is a 5' promoter selected from the group consisting of the RuBisCO 5' promoter and the CAB2 promoter.

33. The method of claim 26 wherein said at least one vector further comprises a sterility operon that renders mature plants incapable of reproduction.

34. The method of claim 26 wherein said at least one vector further comprises a targeting sequence such that expressed polypeptides are directed to a specific organelle.

35. The method of claim 26 wherein said at least one vector further comprises at least one selection sequence comprising at least one gene conferring resistance to an antibiotic.

36. A transgenic bioluminescent plant, comprising:
a plant cell comprising a recombinant DNA; and
wherein said recombinant DNA comprises a lux gene encoding a luciferase, a lux gene encoding a luciferin that is compatible with said luciferase, and at least one light inducible promoter operably linked to at least one of said lux genes.

37. The plant of claim 36 wherein said lux genes are selected from a foreign genome containing a lux operon.

38. The plant of claim 37 wherein said foreign genome is selected from the group of bacteria consisting of genera *Vibrio, Photobacterium,* and *Xenorhabdus.*

39. The plant of claim 36 wherein said lux gene encoding a luciferase comprises luxA and luxB, and said lux gene encoding a luciferin comprises luxC, luxD, and luxE.

40. The plant of claim 36 wherein said recombinant DNA further comprises at least one gene encoding a flavin reductase.

41. The plant of claim 40 wherein said gene encoding a flavin reductase is an frp gene selected from a foreign genome.

42. The plant of claim 36 wherein said recombinant DNA further comprises at least one internal ribosome entry site.

43. The plant of claim 36 wherein said at least one light inducible promoter is the RuBisCO 5' promoter or the CAB2 promoter.

44. The plant of claim 36 wherein said recombinant DNA further comprises a sterility operon that renders the plant incapable of reproduction.

45. The plant of claim 36 wherein said recombinant DNA further comprises a targeting sequence such that expressed polypeptides are directed to a specific organelle.

46. The plant of claim 36 wherein said recombinant DNA further comprises a selection sequence comprising at least one gene conferring resistance to an antibiotic.

47. The plant of claim 36 wherein said recombinant DNA further comprises at least one gene encoding a phototransformative protein and at least one means for regulation of expression of said gene encoding a phototransformative protein.

48. The plant of claim 47 wherein said gene encoding a phototransformative protein is a lux gene selected from the group of bacteria consisting of genera *Vibrio, Photobacterium,* and *Xenorhabdus.*

* * * * *

UNITED STATES PATENT AND TRADEMARK OFFICE
CERTIFICATE OF CORRECTION

PATENT NO. : 7,663,022 B1  
APPLICATION NO. : 11/419108  
DATED : February 16, 2010  
INVENTOR(S) : Bruce Eric Hudkins Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 506 days.

Signed and Sealed this

Thirtieth Day of November, 2010

David J. Kappos  
*Director of the United States Patent and Trademark Office*

SEQUENCE LISTING

```
<160> NUMBER OF SEQ ID NOS: 10

<210> SEQ ID NO 1
<211> LENGTH: 176
<212> TYPE: DNA
<213> ORGANISM: Artificial
<220> FEATURE:
<223> OTHER INFORMATION: Synthetic internal ribosome entry site

<400> SEQUENCE: 1
ggatccgtcg acgaattcgt cgattcggtt gcagcattta aagcggttga caactttaaa      60
agaaggaaaa agaaggttga agaaaagggt gtagtaagta agtataagta cagaccggag     120
aagtacgccg gtcctgattc gtttaatttg aaagaagaaa atgtcccggg ctgcag         176

<210> SEQ ID NO 2
<211> LENGTH: 27
<212> TYPE: DNA
<213> ORGANISM: Artificial
<220> FEATURE:
<223> OTHER INFORMATION: Synthetic primer sequence C forward

<400> SEQUENCE: 2
ggtctagaca gtttaaaaaa gcagtct                                          27

<210> SEQ ID NO 3
<211> LENGTH: 28
<212> TYPE: DNA
<213> ORGANISM: Artificial
<220> FEATURE:
<223> OTHER INFORMATION: Synthetic primer sequence C reverse

<400> SEQUENCE: 3
ggggatccct tgatgatgtg atcaatcg                                         28

<210> SEQ ID NO 4
<211> LENGTH: 28
<212> TYPE: DNA
<213> ORGANISM: Artificial
<220> FEATURE:
<223> OTHER INFORMATION: Synthetic prmier sequence D forward

<400> SEQUENCE: 4
ggcccgggtg tcccatagtt aaaggaaa                                         28

<210> SEQ ID NO 5
<211> LENGTH: 28
<212> TYPE: DNA
<213> ORGANISM: Artificial
<220> FEATURE:
<223> OTHER INFORMATION: Synthetic primer sequence D reverse

<400> SEQUENCE: 5
```

```
gggaattcat ccttttttgg tgattctg                                        28

<210> SEQ ID NO 6
<211> LENGTH: 28
<212> TYPE: DNA
<213> ORGANISM: Artificial
<220> FEATURE:
<223> OTHER INFORMATION: Synthetic primer sequence E forward

<400> SEQUENCE: 6
ggctcgagtt aggtattact ggagaggg                                        28

<210> SEQ ID NO 7
<211> LENGTH: 28
<212> TYPE: DNA
<213> ORGANISM: Artificial
<220> FEATURE:
<223> OTHER INFORMATION: Synthetic primer sequence E reverse

<400> SEQUENCE: 7
gggtcgactg aaactctacc atcaacaa                                        28

<210> SEQ ID NO 8
<211> LENGTH: 28
<212> TYPE: DNA
<213> ORGANISM: Artificial
<220> FEATURE:
<223> OTHER INFORMATION: Synthetic primer sequence frp forward

<400> SEQUENCE: 8
ggctgcaggc tcccaataaa tgccgtta                                        28

<210> SEQ ID NO 9
<211> LENGTH: 28
<212> TYPE: DNA
<213> ORGANISM: Artificial
<220> FEATURE:
<223> OTHER INFORMATION: Synthetic primer sequence frp reverse

<400> SEQUENCE: 9
ggactagttg gcagcgtatg gtcaaaat                                        28

<210> SEQ ID NO 10
<211> LENGTH: 2505
<212> TYPE: DNA
<213> ORGANISM: Vibrio fischeri
<300> PUBLICATION INFORMATION:
<301> AUTHORS: K. Okumura, L. Chlumsky, T.O. Baldwin & C.I. Kado
<302> TITLE: Enhanced stable expression of a Vibrio luciferase under the
       control of the omega-translational enhancer in transgenic plants
<303> JOURNAL: World Journal of Microbiology and Biotechnology
<304> VOLUME: 8
<306> PAGES: 638-644
<307> DATE: 1992

<400> SEQUENCE: 10
ggatcccaag ctttattttt acaacaatta ccttacaatt actatttaca attacagtcg      60
actttatcga gcctgatttt gaacaactca ccatcgcgac tgtgaatgaa cgtcgcttga     120
aagcggaaat tgaaagccgt acgcaagaaa tggcttaggt cttatcgtaa taccaacaaa     180
taaggaaatg ttatgaaatt tggaaacttc cttctcactt atcagccacc tgagctatct     240
cagaccgaag tgatgaagcg attggttaat ctgggcaaag cgtctgaagg ttgtggcttc     300
gacaccgttt ggttgctaga gcaccacttc actgaatttg ggttgttagg gaatccttat     360
```

-continued

```
gttgctgccg cacacctatt agctgcgaca gaaacgctca acgttggcac tgcagctatc    420
gtattgccga ctgcccatcc ggttccacaa gcagaagacg taaacctact ggatcaaatg    480
tcaaaaggac gattccgttt tggtatttgt cgcggtttgt acgataaaga ttttcgtgtc    540
tttggtacag acatggataa cagccgagcc ttaatggact gttggtatga cttgatgaaa    600
gaaggcttca atgaaggcta tatcgcggcg gataacgaac atattaagtt cccgaaaatc    660
caactgaatc catcggctta cacacaaggt ggtgctcctg tttatgtcgt cgcggagtca    720
gcatcaacga cagaatgggc tgcagagcgt ggcctaccaa tgattctaag ctggatcatc    780
aacactcacg agaagaaagc gcagcttgat ctttacaacg aagtcgcgac tgaacatggc    840
tacgatgtga ctaagattga ccactgtttg tcttacatca cctccgtcga tcatgactca    900
aatagagcca aagatatttg ccgcaacttc ttgggccatt ggtacgactc atacgtgaat    960
gccaccaaga tttttgacga ctctgaccaa acaaaaggtt acgacttcaa taaaggtcaa   1020
tggcgtgatt ttgtgttgaa aggccacaaa gacaccaatc gccgaattga ttacagctac   1080
gaaatcaacc cagtagggac gcctgaagag tgtatcgcga ttatccagca agatattgat   1140
gcgacgggta ttgacaatat ttgttgtggt tttgaagcaa acggttctga agaagaaatt   1200
atcgcatcta tgaagctatt ccagtctgat gtgatgccat atctcaaaga aaaacagatc   1260
ttaagtattg ttttaaacag gctcgagcat tcgacaaaag tgttagtgga gccacgcgcg   1320
ccagaatcca gaacttcgaa atttggatta ttcttcctca attttatgaa ttcaaagcgt   1380
tcttctgatc aagtcatcga agaaatgtta gataccgcac attacgtaga tcagttgaag   1440
tttgacacgt tggctgttta cgaaaaccat ttctcgaaca atggtgtggt tggtgcccca   1500
ctaacagtgg ctggtttttt acttggtatg acaaagaacg ccaaagtggc ttcgttgaat   1560
cacgtcatta ccacgcatca tccagtacgt gtggcggaag aagcgtgtct acttgaccaa   1620
atgagtgaag gccgtttttgc ctttggcttt agtgattgtg aaaagagtgc acatatgcgc   1680
ttctttaatc gaccaacgga ttctcagttt cagttgttca gtgagtgtca caagatcatc   1740
aatgatgcat tcactactgg gtactgccat ccaaacaatg attttttatag ttttcctaaa   1800
atctccgtta acccacacgc gttcactgaa ggcggtcctg cgcaatttgt gaatgcgacg   1860
agcaaagaag tggttgaatg ggcggctaag ttagggcttc cactcgtgtt tagatgggac   1920
gactcaaacg ctcaaagaaa agaatacgcc cgtttgtacc acgaagttgc tcaggcacat   1980
ggtgtcgatg ttagtcaggt tcgacacaag ctgacgctgc tggtcaacca aaatgtagat   2040
ggtgaagcag caagggcaga agctcgcgtg tatttggaag agtttgtccg tgaatcttac   2100
tcaaataccg actttgagca aaaaatggga gagctgttgt cagaaaatgc catcggtact   2160
tatgaagaaa gtactcaggc agcgcgagtt gcgattgagt gttgtggtgc cgcggaccta   2220
ttgatgtctt ttgagtcgat ggaagataaa gcgcagcaaa gagcggttat cgatgtggta   2280
aacgccaaca tcgtcaaata ccactcgtaa cgtttaactg atgctgaagg ggcagcgatg   2340
ccccttatat caccattctt ttcgccgata gcgctaacta atagaggcat ttatatggac   2400
gtactttcag cggttaagca ggaaaacatc gcagcgagca cagaaatcga tgacttgatt   2460
ttcatgggaa ctcctcagca atggtcattg caggaacaaa aacag                   2505
```